US009968928B2

(12) United States Patent
Bru Gibert et al.

(10) Patent No.: US 9,968,928 B2
(45) Date of Patent: *May 15, 2018

(54) PLURALITY OF REACTION CHAMBERS IN A TEST CARTRIDGE

(71) Applicant: STAT-DIAGNOSTICA & INNOVATION, S.L., Barcelona (ES)

(72) Inventors: Rafael Bru Gibert, Barcelona (ES); Jordi Carrera Fabra, Barcelona (ES); Anna Comengés Casas, Barcelona (ES); José Antonio Garcia Sánchez, Villanova del Vallés (ES)

(73) Assignee: STAT-Diagnostica & Innovation, S.L., Barcelona (ES)

( * ) Notice: Subject to any disclaimer, the term of this patent is extended or adjusted under 35 U.S.C. 154(b) by 175 days.

This patent is subject to a terminal disclaimer.

(21) Appl. No.: 14/743,893

(22) Filed: Jun. 18, 2015

(65) Prior Publication Data

US 2015/0284774 A1 Oct. 8, 2015

Related U.S. Application Data

(63) Continuation of application No. 13/837,007, filed on Mar. 15, 2013, now Pat. No. 9,063,121.
(Continued)

(51) Int. Cl.
*C12Q 1/68* (2018.01)
*C12P 19/34* (2006.01)
(Continued)

(52) U.S. Cl.
CPC ............. *B01L 3/502* (2013.01); *B01L 3/5027* (2013.01); *C12Q 1/6806* (2013.01); *G01N 21/75* (2013.01);
(Continued)

(58) Field of Classification Search
CPC ..... B01L 2200/0605; B01L 2300/0627; B01L 2300/0848; B01L 2300/0861;
(Continued)

(56) References Cited

U.S. PATENT DOCUMENTS

| 5,380,437 | A | 1/1995 | Bertoncini |
| 5,786,182 | A | 7/1998 | Catanzariti et al. |

(Continued)

FOREIGN PATENT DOCUMENTS

| AU | 758407 B2 | 7/1999 |
| AU | 2003200701 B2 | 5/2003 |

(Continued)

OTHER PUBLICATIONS

International Preliminary Report on Patentability and Written Opinion of the International Search Authority directed to related International Patent Application No. PCT/EP2013/059692, dated Nov. 11, 2014; 8 pages.
(Continued)

*Primary Examiner* — Young J Kim
(74) *Attorney, Agent, or Firm* — Sterne, Kessler, Goldstein & Fox, P.L.L.C.

(57) ABSTRACT

A fluidic testing system is presented that includes a plurality of test chambers, a plurality of inlet channels, and a fluidic network that connects the inlet channels to one or more other chambers. The plurality of test chambers are each characterized by a length and a hydraulic diameter. The length of each test chamber is aligned substantially parallel to a gravity vector. Each of the test chambers has only one opening disposed along the length of the corresponding test chamber. Additionally, each of the test chambers is coupled via its respective opening to only one of the plurality of inlet channels.

10 Claims, 11 Drawing Sheets

Related U.S. Application Data

(60) Provisional application No. 61/644,858, filed on May 9, 2012.

(51) Int. Cl.
  *B01L 3/00* (2006.01)
  *G01N 21/75* (2006.01)
  *G01N 33/50* (2006.01)
  *G01N 33/53* (2006.01)

(52) U.S. Cl.
  CPC ......... *G01N 33/50* (2013.01); *G01N 33/5306* (2013.01); *B01L 2200/0605* (2013.01); *B01L 2300/0627* (2013.01); *B01L 2300/087* (2013.01); *B01L 2300/0848* (2013.01); *B01L 2300/0861* (2013.01); *B01L 2300/0864* (2013.01); *B01L 2300/12* (2013.01); *B01L 2300/18* (2013.01); *B01L 2300/1822* (2013.01); *B01L 2300/1827* (2013.01); *B01L 2400/0475* (2013.01)

(58) Field of Classification Search
  CPC ....... B01L 2300/0864; B01L 2300/087; B01L 2300/12; B01L 2300/18; B01L 2300/1822; B01L 2300/1827; B01L 2400/0475; B01L 3/502
  See application file for complete search history.

(56) References Cited

U.S. PATENT DOCUMENTS

| | | | |
|---|---|---|---|
| 6,124,138 | A | 9/2000 | Woudenberg et al. |
| 7,320,777 | B2 | 1/2008 | Bordenkircher et al. |
| 8,133,703 | B2 * | 3/2012 | Ching .................... B01L 3/502 435/91.2 |
| 9,063,121 | B2 | 6/2015 | Bru Gilbert et al. |
| 9,176,126 | B2 | 11/2015 | Holmes et al. |
| 2002/0068358 | A1 | 6/2002 | Campbell et al. |
| 2003/0040021 | A1 | 2/2003 | Clark et al. |
| 2003/0219713 | A1 | 11/2003 | Valencia et al. |
| 2005/0158781 | A1 | 7/2005 | Woudenberg et al. |
| 2005/0161669 | A1 * | 7/2005 | Jovanovich ....... B01L 3/502715 257/48 |
| 2007/0025875 | A1 | 2/2007 | Peters et al. |
| 2007/0026439 | A1 | 2/2007 | Faulstitch et al. |
| 2007/0099290 | A1 | 5/2007 | Iiida et al. |
| 2007/0189927 | A1 | 8/2007 | Ballhorn et al. |
| 2007/0217963 | A1 | 9/2007 | Elizarov et al. |
| 2009/0155128 | A1 | 6/2009 | Peters et al. |
| 2009/0197274 | A1 | 8/2009 | Takagi |
| 2009/0269800 | A1 | 10/2009 | Covey et al. |
| 2010/0323454 | A1 | 12/2010 | Saiki et al. |
| 2015/0283542 | A1 | 10/2015 | Bru Gibert et al. |
| 2015/0284771 | A1 | 10/2015 | Bru Gibert et al. |
| 2015/0284772 | A1 | 10/2015 | Bru Gibert et al. |
| 2015/0284773 | A1 | 10/2015 | Bru Gibert et al. |

FOREIGN PATENT DOCUMENTS

| | | | |
|---|---|---|---|
| CN | 101194155 | A | 6/2008 |
| CN | 101883985 | A | 11/2010 |
| EP | 0 889 751 | B1 | 9/1999 |
| EP | 0 9635 45 | B1 | 5/2011 |
| JP | 2002-505946 | A | 2/2002 |
| JP | 2006-126011 | A | 5/2006 |
| JP | 2008-534972 | A | 8/2008 |
| JP | 2009-178146 | A | 8/2009 |
| JP | 2011-527434 | A | 10/2011 |
| RU | 2256167 | C2 | 7/2005 |
| WO | WO 2004/028692 | A2 | 4/2004 |
| WO | WO 2010/004436 | A2 | 1/2010 |

OTHER PUBLICATIONS

Abstract of App. No. CN 101194155 A, filed Jun. 4, 2008; 1 page.
Chinese Office Action dated Oct. 10, 2015 directed to App. No. 201380034569.3, filed May 9, 2013; 6 pages.
Translation of Chinese Office Action dated Oct. 10, 2015 directed to App. No. 201380034569.3, filed May 9, 2013; 6 pages.
International Search Report for International Application No. PCT/EP2013/059692, European Patent Office, Netherlands, dated Nov. 20, 2013; 10 pages.
U.S. Appl. No. 14/743,513, Bru Gibert et al., "Plurality of Reaction Chambers in a Test Cartridge," filed Jun. 18, 2015.
U.S. Appl. No. 14/743,676, Bru Gibert et al., "Plurality of Reaction Chambers in a Test Cartridge," filed Jun. 18, 2015.
U.S. Appl. No. 14/743,552, Bru Gibert et al., "Plurality of Reaction Chambers in a Test Cartridge," filed Jun. 18, 2015.
U.S. Appl. No. 14/743,310, Bru Gibert et al., "Plurality of Reaction Chambe Rs in a Test Cartridge," filed Jun. 18, 2015.
English Abstract for Japanese Patent Publication No. JP 2002-505946 A, published Feb. 26, 2002, from https://worldwide.espacenet.com, 1 page.
English Abstract for Japanese Patent Publication No. JP 2006-126011 A, published May 18, 2006, from https://worldwide.espacenet.com, 2 pages.
English Abstract for Japanese Patent Publication No. JP 2008-534972 A, published Aug. 28, 2008, from https://worldwide.espacenet.com, 1 page.
English Abstract for Japanese Patent Publication No. JP 2009-178146 A, published Aug. 13, 2009, from https://worldwide.espacenet.com, 2 pages.
English Abstract for Japanese Patent Publication No. JP 2011-527434 A, published Oct. 27, 2011, from https://worldwide.espacenet.com, 1 page.
English Abstract for Russian Patent Publication No. RU 2256167 C2, published Jul. 10, 2005, from https://worldwide.espacenet.com, 1 page.
Chinese Office Action dated Apr. 1, 2017 directed to App. No. 201610103877.2, filed May 9, 2013; 6 pages.
Translation of Chinese Office Action dated Apr. 1, 2017 directed to App. No. 201610103877.2, filed May 9, 2013; 6 pages.
Japanese Office Action dated Apr. 4, 2017 directed to App. No. 2015-510826, filed May 9, 2013, 5 pages.
Translation of Japanese Office Action dated Apr. 4, 2017 directed to App. No. 2015-510826, filed May 9, 2013, 8 pages.
Russian Office Action dated Jun. 9, 2017 directed to App. No. 2014144122/05, filed May 9, 2013, 7 pages.
Translation of Russian Office Action dated Jun. 9, 2017 directed to App. No. 2014144122/05, filed May 9, 2013, 6 pages.

* cited by examiner

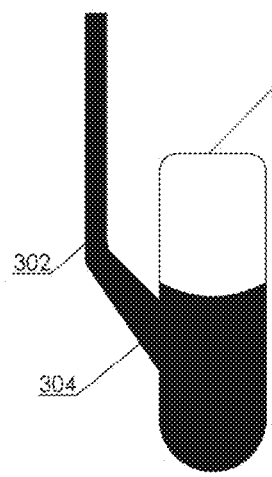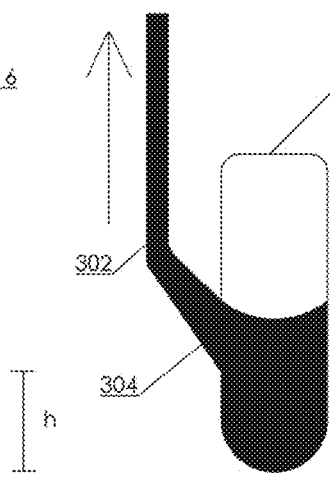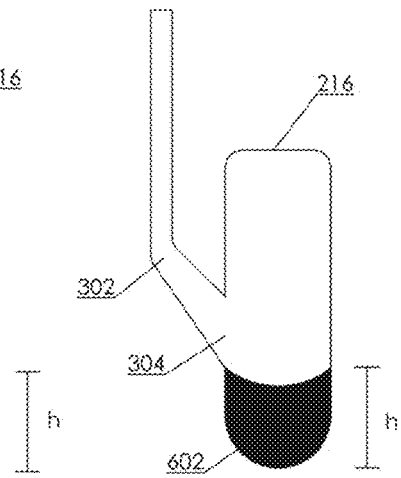
Fig. 6A            Fig. 6B            Fig. 6C
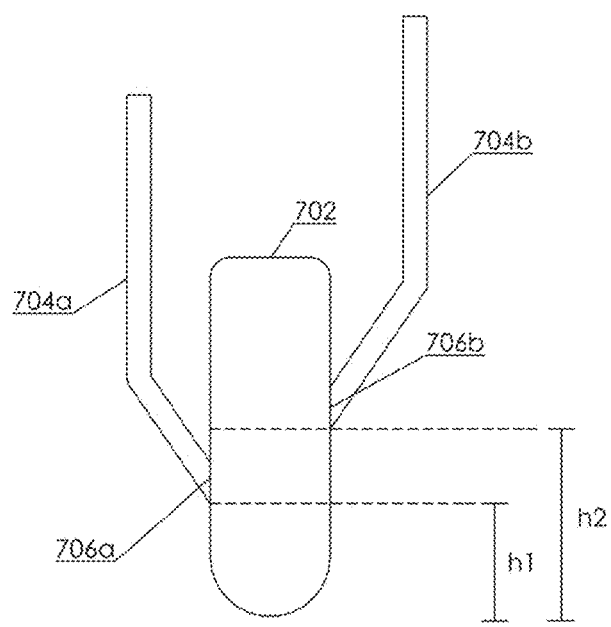
Fig. 7

1400

Flow liquid through each of a plurality of channels up to a liquid sensing area in each channel, thus setting a pre-determined amount of liquid in each channel — 1402

Flow only the pre-determined amount of liquid into respective chambers coupled to each of the channels — 1404

Fig. 14

PLURALITY OF REACTION CHAMBERS IN A TEST CARTRIDGE

CROSS-REFERENCE TO RELATED APPLICATIONS

This application is a continuation of U.S. application Ser. No. 13/837,007 filed on Mar. 15, 2013, which claims the benefit under 35 U.S.C. § 119(e) to provisional application No. 61/644,858 filed on May 9, 2012, the disclosures of which are each incorporated by reference herein in their entireties.

BACKGROUND

Field

Embodiments of the present invention relate to the field of clinical diagnostic tools.

Background

Given the complexity of the automation of molecular testing and immunoassay techniques, there is a lack of products that provide adequate performances to be clinically usable in near patient testing settings. Typical molecular testing includes various processes involving the correct dosage of reagents, sample introduction, lysis of cells to extract DNA or RNA, purification steps, and amplification for its subsequent detection. Even though there are central laboratory robotic platforms that automate some of these processes, for many tests requiring a short turnaround time, the central laboratory cannot provide the results in the needed time requirements.

However, it is difficult to implement systems in a clinical setting that provide accurate, trustworthy results at a reasonable expense. Given the complicated nature of various molecular testing techniques, the results are prone to error if the testing parameters are not carefully controlled or if the environmental conditions are not ideal. For example, existing instrumentation for PCR techniques has experienced high entry barriers for clinical diagnosis applications due to the background generated by exogenous sources of DNA. In the case of specific tests of pathogens, the predominant source of contamination is a result of previous reactions carried out in pipettes, tubes, or general laboratory equipment. Additionally, the use of molecular techniques for detection of microbial pathogens can produce false negatives. The false negatives may result from, for example: improper disposal of agents that inhibit the Polymerase Chain Reaction (PCR) such as hemoglobin, urine or sputum; inefficient release of DNA from cells; or low efficiency in extraction and purification of DNA or RNA.

The fact that molecular techniques have exceptional sensitivity levels at concentrations lower than the previous reference methods makes it rather difficult to obtain clinically relevant conclusions, while avoiding erroneous calls with false positives. To minimize this problem, especially for the detection of pathogen microorganisms, tests should have quantification capability. It has therefore become increasingly necessary to perform multiplexed assays and arrays of tests to consolidate enough data to make confident conclusions. As an example, one of the main limitations of existing PCR-based tests is the inability to perform amplifications of different target genes simultaneously. While techniques such as microarrays provide very high multiplexing capacity, their main limitation is the low speed in obtaining the results, which often have no positive impact on patient management.

BRIEF SUMMARY

A fluidic testing system which includes a plurality of test chambers is presented. Simultaneous fluid control of each testing site can reduce testing time and enhance the probability of obtaining repeatable results among the various testing sites.

In an embodiment, a single-port fluidic testing system includes a plurality of test chambers, each characterized by a length and a hydraulic diameter. Each of the plurality of test chambers has only one opening disposed along the length of the corresponding test chamber. The fluidic testing system further includes a first inlet channel and a plurality of fluid splitting elements. The fluid splitting elements split an initial liquid flowing down the first inlet channel into a plurality of second inlet channels. Each of the plurality of test chambers is coupled via its respective opening to only one of the plurality of second inlet channels.

An example method is described. The method includes flowing an initial amount of liquid down a first inlet channel of a single-port fluidic testing system. The initial amount of liquid is split into a plurality of second inlet channels, each second inlet channel coupled to a plurality of test chambers, wherein each of the plurality of test chambers has only one opening disposed along a length of the chamber. The method further includes filling each of the test chambers with a final amount of liquid, the final amount being substantially equal in each of the test chambers and summing from each test chamber to equal the initial amount of liquid.

In another embodiment, a fluidic testing system includes a plurality of test chambers, a plurality of inlet channels, and a fluidic network that connects the inlet channels to one or more other chambers. The test chambers each have a length and a hydraulic diameter. The length of each test chamber is aligned substantially parallel to a gravity vector. Each of the test chambers has only one opening disposed along the length of the corresponding test chamber. Additionally, each of the test chambers is coupled via its respective opening to only one of the plurality of inlet channels.

Another example method is described. The method includes flowing liquid through a plurality of inlet channels, each inlet channel coupled to a plurality of test chambers. A length of each test chamber is aligned substantially parallel to a gravity vector, and each of the test chambers has only one opening disposed along the length of the chamber. The method further includes filling each of the plurality of test chambers with the liquid up to a threshold amount. The method further includes drawing the liquid away from each of the test chambers through the inlet channels to leave behind a predetermined amount of the liquid within each test chamber.

Another example method is described. The method includes flowing a first liquid through a first inlet channel coupled to a first opening disposed along a length of a test chamber at a first height. The length of the test chamber is aligned substantially parallel to a gravity vector. The method further includes filling the test chamber with the first liquid up to a first threshold amount. The first liquid is drawn away from the test chamber through the first inlet channel, and leaves behind a first predetermined amount of the first liquid within the test chamber. The method further includes flowing a second liquid through a second inlet channel coupled to a second opening disposed along the length of the test chamber at a second height. The second height is greater than the first height. The method further includes filling the test chamber with the second liquid up to a second threshold amount. The second liquid is drawn away from the test chamber through the second inlet channel, and leaves behind a second predetermined amount of the second liquid within the test chamber.

Another example method is described. The method includes flowing liquid through each of a plurality of channels up to a liquid sensing area disposed in each channel, thus setting a pre-determined amount of liquid within each of the plurality of channels. The method further includes flowing only the pre-determined amount of liquid within each of the plurality of channels into respective chambers coupled to each of the channels.

BRIEF DESCRIPTION OF THE DRAWINGS/FIGURES

The accompanying drawings, which are incorporated herein and form a part of the specification, illustrate embodiments of the present invention and, together with the description, further serve to explain the principles of the invention and to enable a person skilled in the pertinent art to make and use the invention.

FIG. 1 is a graphical representation of a test cartridge system, according to an embodiment.

FIG. 2 displays a side view of the test cartridge system, according to an embodiment.

FIG. 3 illustrates a test chamber, according to an embodiment.

FIGS. 4A-C illustrate operation of the test chamber, according to an embodiment.

FIG. 5 illustrates a plurality of test chambers, according to an embodiment.

FIGS. 6A-C illustrate another operation of the test chamber, according to an embodiment.

FIG. 7 illustrates another test chamber, according to an embodiment.

FIGS. 11-14 illustrate example chamber filling methods, according to embodiments.

Figure 1:
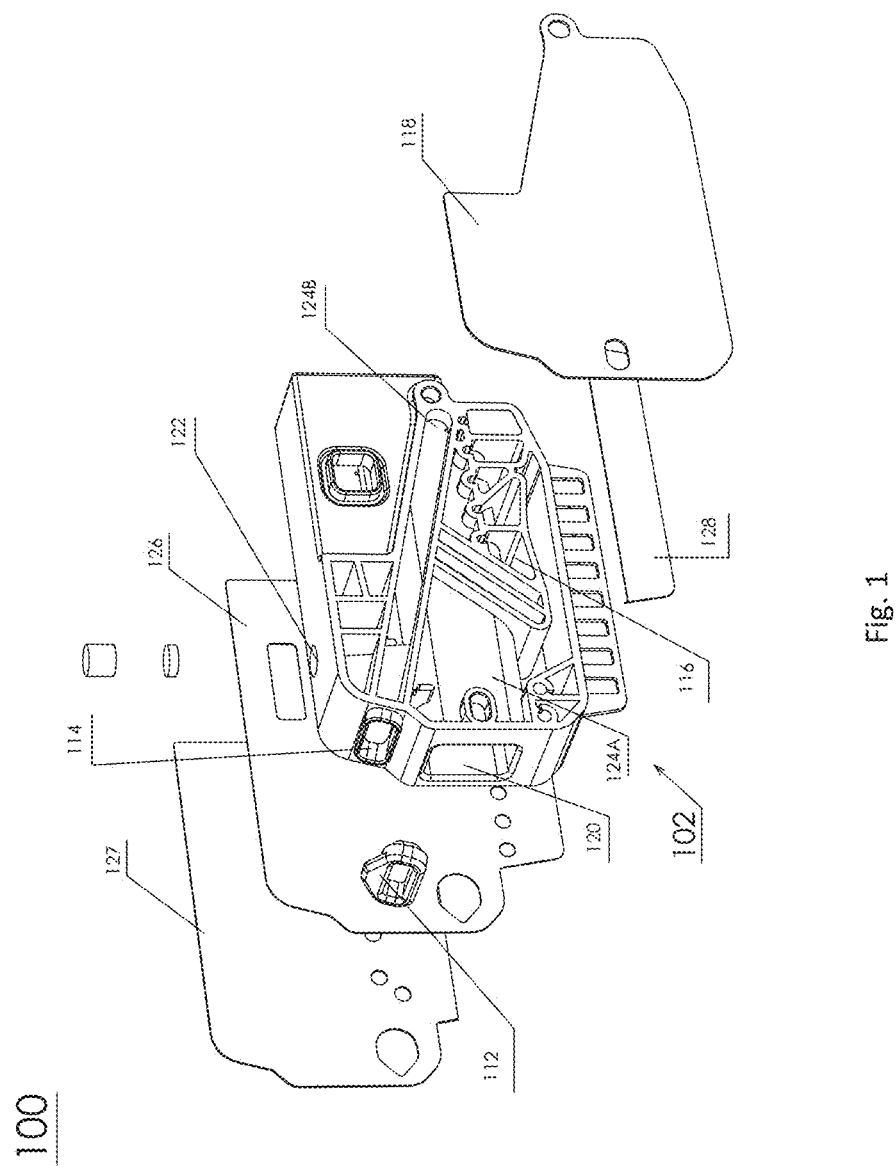

Embodiments of the present invention will be described with reference to the accompanying drawings.

DETAILED DESCRIPTION

Although specific configurations and arrangements are discussed, it should be understood that this is done for illustrative purposes only. A person skilled in the pertinent art will recognize that other configurations and arrangements can be used without departing from the spirit and scope of the present invention. It will be apparent to a person skilled in the pertinent art that this invention can also be employed in a variety of other applications.

It is noted that references in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure or characteristic is described in connection with an embodiment, it would be within the knowledge of one skilled in the art to effect such feature, structure or characteristic in connection with other embodiments whether or not explicitly described.

Embodiments described herein relate to a test cartridge system for performing a variety of molecular tests, such as immunoassays, PCR, DNA hybridization, etc. In an embodiment, the test cartridge integrates all of the components necessary to perform such tests into a single, disposable package. The test cartridge may be configured to be analyzed by an external measurement system which provides data related to the reactions that take place within the test cartridge. In an embodiment, the test cartridge includes a plurality of test chambers with a transparent window to perform optical detection with each test chamber.

In one example, a single test cartridge may be used to perform an array of immunoassays with a given sample. The test cartridge contains all of the necessary buffers, reagents, and labels held in sealed chambers integrated into the cartridge to perform the immunoassays.

In another example, a single test cartridge may be used to perform PCR. The DNA may be purified from the rest of a sample via a filter incorporated into the test cartridge. The sample may be extruded through the filter while a separately stored elution liquid may remove the DNA and bring it into another chamber to begin the process of temperature cycling.

One of the main limitations of molecular diagnostic instrumentation is the problem associated with contamination such as cross-contamination, carry-over contamination, etc. Embodiments described herein substantially eliminate by design the contamination of samples to the instrument.

In one embodiment, the test cartridge offers a self-contained liquid sealed during the manufacturing process. The reagents and the sample do not enter into contact with the environment or with any part of the instrument. This feature of the test cartridge is also important for many laboratories and hospitals to safely dispose of the products after their use.

In order to perform an array of tests, the test cartridge contains a plurality of test chambers designed to facilitate measuring optical properties of the contents within each test chamber, according to an embodiment. For example, the test chambers each contain a transparent window to allow for either fluorescence or absorbance studies of the contents therein. Additionally, the design of the fluidic arrangement to each test chamber may allow for each chamber to be filled to the same level while using a single pump source.

Further details relating to the components of the test cartridge system, including the test chambers, are described herein with references made to the figures. It should be understood that the illustrations of each physical component are not meant to be limiting and that a person having skill in the relevant art(s) given the description herein would recognize ways to re-arrange or otherwise alter any of the components without deviating from the scope or spirit of the invention.

FIG. 1 illustrates an example test cartridge system 100 with an array of test chambers, according to an embodiment. Although reference will be made herein to the structure of example test cartridge system 100, one of skill in the art will recognize that test chamber embodiments described herein may be used with any number of testing system types and configurations.

Test cartridge system 100 includes a cartridge housing 102. Other components may be considered as well for inclusion in test cartridge system 100, such as an analyzer module or various active components such as pumps or heaters.

Cartridge housing 102 includes a variety of fluidic channels, chambers, and reservoirs. For example, cartridge housing 102 may include a plurality of storage chambers 116 which may contain various buffers or other reagents to be used during an assay or PCR protocol. Storage chambers 116 may be pre-filled with various liquids so that the end user will not need to fill storage chambers 116 before placing test cartridge system 100 into an analyzer. In another example, the reagents are freeze-dried before being placed in storage chambers 116. Cartridge housing 102 may further include one or more processing chambers 124a-b connected to fluidic channels along a side of cartridge housing 102. Processing chambers 124a-b may be used for a variety of processing and/or waste applications.

Samples are introduced into cartridge housing 102 via sample port 114, according to an embodiment. In an example, sample port 114 receives solid, semi-solid, or liquid samples. In another embodiment, cartridge housing 102 includes more than one inlet to introduce samples.

The various chambers and channels around cartridge housing 102 may be sealed via the use of covers 118, 126, 127, and 128. The covers may be films capable of sealing the fluid within cartridge housing 102. In another example, the covers may be plastic panels. In an example, one or more of the covers are transparent. Additionally, one or more of the covers may be thermally controlled for heating portions of housing 102.

The integrated test cartridge system 100 allows a user to place a sample into, for example, sample port 114, then place test cartridge system 100 into an analyzer. In embodiments, the reaction steps to be performed including, for example, purification, lysing, mixing, binding, labeling and/or detecting can all be performed within test cartridge system 100 via interaction with the analyzer without any need for the end user to intervene. Additionally, since all of the liquids remain sealed within test cartridge system 100, after the test is completed, test cartridge system 100 may be removed from the analyzer and safely disposed of without contamination of the analyzer.

Figure 2:
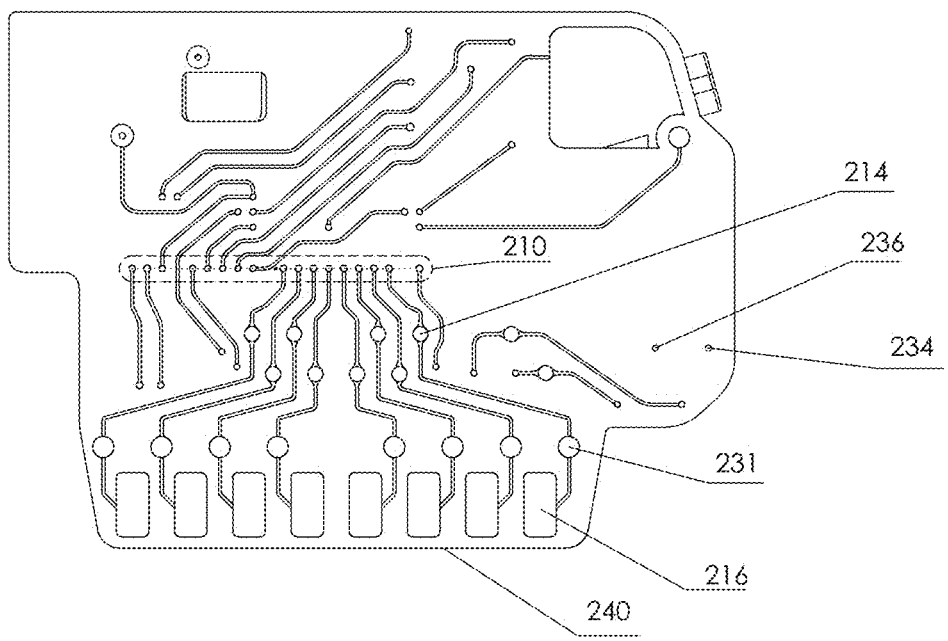

FIG. 2 illustrates a side view of cartridge housing 102, according to an embodiment. The description of cartridge housing 102 is set forth to describe features that may be present on cartridge housing 102, but should not be limiting as to the placement or dimensional properties of the features.

FIG. 2 illustrates a fluidic network and a series of ports which extend into cartridge housing 102. The fluidic network may connect to one or more of storage chambers 116 and/or processing chambers 124a-b of cartridge housing 102. These chambers may be disposed on the opposite side of cartridge housing 102 from the side illustrated in FIG. 2. In an embodiment, the fluidic network also connects to a series of test chambers 216.

Each fluidic channel may also be designed to terminate at a port which will interface with the ports or valve regions on a moveable transfer module (not shown) within housing 102. A plurality of ports 210 allow fluid to flow to any chamber of housing 102, according to an embodiment. Plurality of ports 210 may act as either inlet ports for liquid to be drawn into an inner chamber within cartridge housing 102, or as outlet ports for liquid to be expelled from the inner chamber to the fluidic network of cartridge housing 102. For example, liquid may be pressurized to flow through the second to the right port of liquid ports 210 and down into the far right test chamber 216. Furthermore, liquid may be drawn back from the far right test chamber 216 and into the second to the right port of liquid ports 210 via an applied vacuum pressure.

Test chambers 216 may be shaped similarly, for example, to a centrifuge tube. In one embodiment, liquid may be drawn into test chambers 216 to mix with reagents that have been pre-loaded into each test chamber. For example, each test chamber may be loaded with different primers and probes for a PCR process, and liquid may be drawn into each test chamber to create distinct mixtures in each chamber. The reagents may be freeze-dried before being loaded into test chambers 216. In another embodiment, test chambers 216 are also used for sample detection. Detection may occur using an external optical source and photodetector coupled to an analyzer in which test cartridge system 100 is placed. Thus, any walls or covers of test chambers 216 may be transparent to allow for optical detection. In one example, the photodetector measures absorbance through the liquid within the test chamber at one or more wavelengths. In another example, the photodetector measures a fluorescence signal generated from a fluorescent compound within the test chamber. In an embodiment, the fluorescence measurements are taken from beneath test chambers 216. Test chambers 216 may be adapted for other means of detection, e.g., electrochemical, electromechanical, surface plasmon resonance, etc.

A set of smaller channel enlargements 214 are observed upstream from test chambers 216, according to an embodiment. Channel enlargements 214 may act as liquid sensing areas. As such, channel enlargements 214 may be used along with an external optical probe to determine whether or not liquid is present within channel enlargements 214. This determination may be used to activate other functions of test cartridge system 100. In another embodiment, channel enlargements 214 may include integrated sensors, such as a patterned resistive sensor, to indicate the presence or flow rate of the fluid. Additionally, the optical signal detected at a particular channel enlargement 214 monitors the presence of liquid within a corresponding test chamber 216.

The liquid sensing areas in channel enlargements 214 may be used to set pre-determined amounts of liquid to be dosed into each test chamber 216. For example, liquid may be pressurized into each channel separately or simultaneously until the liquid reaches the liquid sensing areas in each channel. In this way, each channel may contain substantially the same amount of liquid filling the channel up to channel enlargement 214. Afterwards, each channel may be separately or simultaneously pressurized to force the pre-determined amount of liquid down into each test chamber 216, according to some embodiments.

A plurality of premixing chambers 231 may also be disposed upstream from test chambers 216, according to an embodiment. Premixing chambers 231 may include dry chemicals, such as frozen or lyophilized analytes. In another example, premixing chambers 231 include dry chemistry beads or biological samples. The biological samples may be freeze dried within premixing chambers 231. Such biological or chemical compounds may be stored in premixing chambers 231 for long periods of time before use. The dimensions of premixing chambers 231 may be designed to specifically fit the size of a dry chemistry bead, usually on the order of a few millimeters in diameter, according to one embodiment. In one example, fluid drawn towards reaction chambers 216 mixes with the samples stored in premixing chambers 231.

At the lower part of cartridge housing 102 in FIG. 2, an optical access area 240 is disposed below test chambers 216, according to an embodiment. Optical access area 240 is designed to be substantially transparent to all wavelengths used during the optical detection process. In one example, each individual test chamber 216 has its own optical access area. In another example, a single optical access area stretches across multiple test chambers 216.

Also illustrated on the side of cartridge housing 102 are a pressure port 236 and a vent port 234, according to an embodiment. Pressure port 236 may be connected to an external pressure source for applying either positive or negative pressure differentials throughout the system, according to an embodiment. Vent port 234 may either be open to the atmosphere or connect to another pressure source. For example, a positive pressure difference may be applied to one port while a negative pressure difference is applied to the other port to force a faster movement of liquid through the coupled channels of the system.

A film or plurality of films may be placed over the series of test chambers 216. The films may be thin enough to still provide adequate sealing while also allowing for easier heating and/or cooling of the contents within test chambers 216 via an external source. For example, the films may have a surface that is thermally controlled by any one of, or a combination of, thermoelectric devices, resistive heaters, and forced air. In one example, the films are polymeric films having a thickness less than 100 microns. In one example, the thermal conductivity of the films is greater than 1 W/mK.

Figure 3:
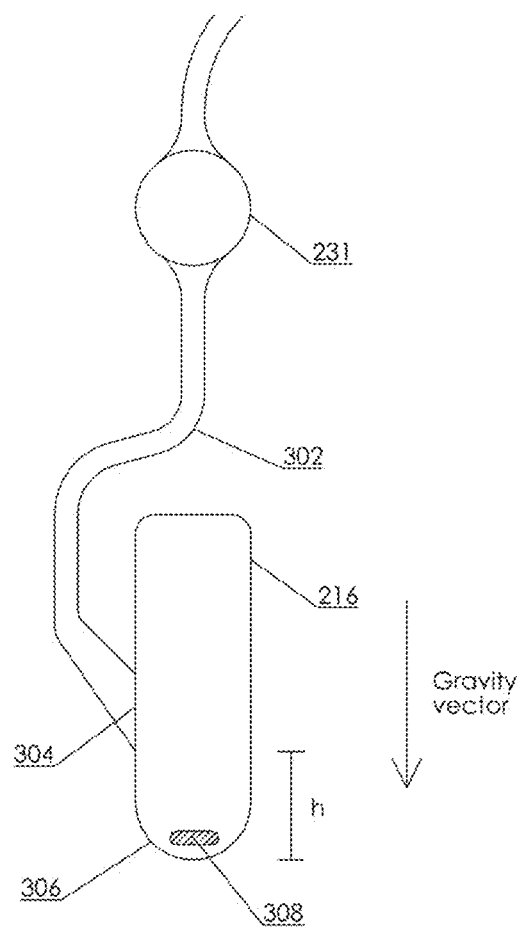

FIG. 3 illustrates a more detailed view of test chamber 216, according to an embodiment. Test chamber 216 includes a single opening 304 disposed along a length of test chamber 216 that couples to an inlet channel 302. Test chamber 216 also has a curved bottom wall 306. Curved bottom wall 306 may be transparent to allow for optical detection from underneath test chamber 216. Test chamber 216 has a large enough hydraulic diameter that gravity influences the fluid flow within test chamber 216. Thus, test chamber 216 is aligned so that its length is substantially parallel to a gravity vector. Due to this alignment, the liquid is influenced by the forces of gravity and fills the chamber from the bottom up.

Test chamber 216 may contain reagents 308. Any number of reagents may be present within reagents 308. Reagents 308 may be present in liquid form or as a freeze-dried pellet. Reagents 308 are re-suspended within the liquid that flows into test chamber 216. In another example, reagents 308 are stored in premixing chamber 231 to mix with fluid upstream from test chamber 216.

An inlet channel 302 couples to test chamber 216 via opening 304. Inlet channel 302 may be one channel of a plurality of channels integrated within cartridge housing 102. Inlet channel 302 provides a fluid path for liquid to flow into test chamber 216 and be drawn from test chamber 216.

In an embodiment, opening 304 is wider than the width of inlet channel 302. The wider opening provides a more controlled entry of liquid into test chamber 216 and also reduces the size of the droplet created by the liquid as it enters into test chamber 216 through opening 304. Each of these factors reduce the probability that the liquid forms a meniscus between the two lateral walls of test chamber 306. The formation of the meniscus makes it difficult to control the amount of liquid within the chamber and causes bubbles to form. The bubbles can disrupt any biological processes to take place within test chamber 216 and cause errors in the optical measurements.

Figures 4A, 4B, 4C:
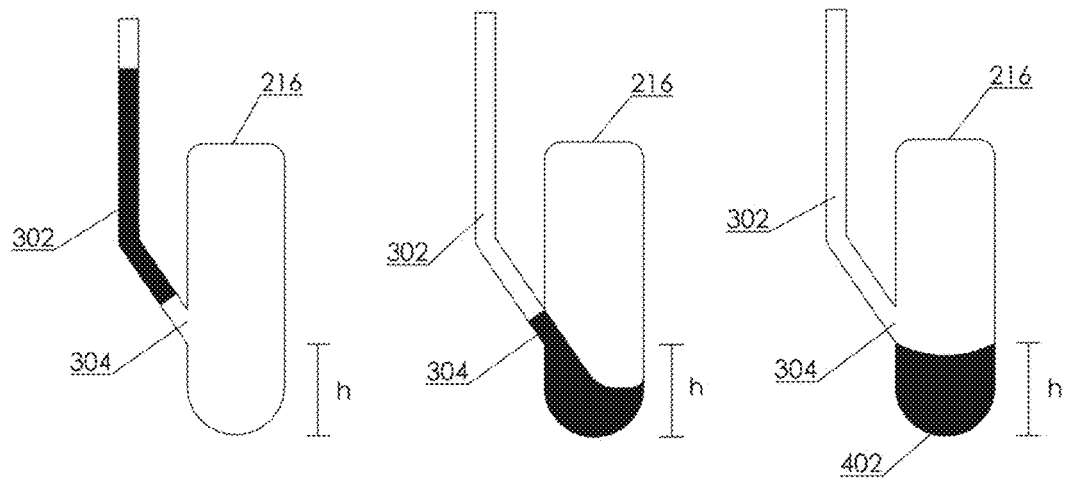

An example operation of test chamber 216 is illustrated in FIGS. 4A-C, according to an embodiment. In FIG. 4A, a pre-determined amount of liquid is disposed within inlet channel 302. The pre-determined amount of liquid is dispensed through opening 304 and into test chamber 216 as illustrated in FIG. 4B. The liquid may be dispensed, for example, via a generated pressure difference.

In one example, the amount of liquid to be dosed into test chamber 216 is chosen so that the resulting liquid level is either at or below a height h, where h is the distance of opening 304 from the bottom of test chamber 216. The resultant liquid 402 is illustrated in FIG. 4C. As a result, any gas in the top portion of test chamber 216 is free to escape via opening 304.

Dosing a pre-determined amount of liquid into test chamber 216 allows the procedure to take place via a single pressurization event. As such, coordinating the filling of multiple test chambers in parallel is simplified.

Figure 5:
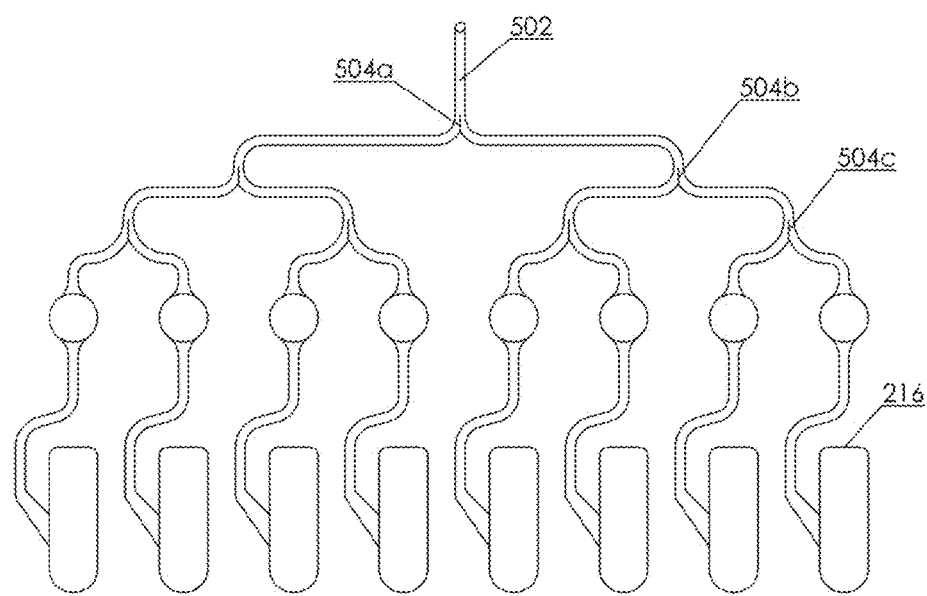

FIG. 5 illustrates an example arrangement for a plurality of test chambers 216, according to an embodiment. A single connecting inlet (or port) 502 is illustrated for coupling the various test chambers 216 to the fluidic network of, for example, test cartridge system 100. In an embodiment, single inlet 502 is coupled to a single port where the single port is the only external opening to the fluidic system.

In the example shown, since only single inlet 502 is provided for dosing liquid into multiple test chambers 216, the fluidic channels include various channel splitters 504a-c. The geometry of channel splitters 504a-c may be chosen so that half of the incoming liquid flows down one path while the other half flows down the other path. Alternatively, the geometry may be chosen to create any ratio of splitting the liquid between the two resulting channels. The plurality of test chambers 216 need not be aligned straight across as illustrated but can be arranged in any fashion that keeps the total path lengths between the single inlet 502 and each of the test chambers 216 equal. The equal path lengths simplify the procedure for dosing controlled amounts of liquid into each test chamber 216.

Channel splitters 504a-c assist in providing an equal amount of liquid to dose into each of test chambers 216. For example, 80 μL of liquid may be introduced via single connecting inlet 502. After going through channel splitter 504a, 504b, and 504c in succession, 10 μL of liquid would be dosed into each test chamber 216. Although this example considers that each channel splitter 504a-c is a 50/50 fluid splitter, this does not need to be the case and any ratio of resulting fluid amounts could be realized amongst the test chambers 216.

The channel arrangement illustrated in FIG. 5 represents a closed fluidic system that allows for dosing to be more easily implemented via a single pressurization event. For example, a positive pressure applied to single connecting inlet 502 may be used to dose a pre-determined amount of liquid into each of test chambers 216 as described previously with regard to FIGS. 4A-C.

FIGS. 6A-C describe an example operation of test chamber 216, according to an embodiment. In FIG. 6A, test chamber 216 is filled with liquid up to a height greater than height h. A positive pressure may be applied to fill chamber 216 up to this point. In an embodiment, a pressure sensor and/or regulator may be included with the system to control the applied pressure and sense when the liquid has reached a threshold amount.

In FIG. 6B, a negative pressure is applied and the liquid is drawn out of test chamber 216 through inlet channel 302. The negative pressure may be applied so that the fluid is drawn out faster than when it flowed into test chamber 216.

In FIG. 6C, liquid is drawn out until the liquid level within test chamber 216 drops below height h. A pre-determined amount 602 of liquid remains within test chamber 216 after the negative pressure is removed. The exact volume of predetermined amount 602 depends on height h of opening 304, the hydraulic diameter of test chamber 216, and the pressure applied during the drawing of the liquid. Using this procedure, a calculated amount of liquid can be dosed into test chamber 216 through only the single inlet channel 302. For example, the amount of liquid left in the chamber may be determined by the point at which the gravitational force and surface tension on the liquid overcome the negative pressure applied to the channel. In one example, the liquid is drawn out of test chamber 216 quickly enough so that no reagents that may be present within test chamber 216 are drawn back through inlet channel 302. Height h may be adjusted for various designs of test chamber 216 to adjust the amount of liquid left behind within test chamber 216.

FIG. 7 illustrates an embodiment of a multi-channel chamber 702. Two inlet channels 704a-b are coupled to multi-channel chamber 702 via openings 706a-b respectively. Each of openings 706a-b are disposed along a length of multi-channel chamber 702 at a height $h_1$ and $h_2$, respectively.

Multi-channel chamber 702 may be used to dose various controlled levels of different liquids within the same chamber. For example, with inlet channel 704b closed off to the atmosphere, a first liquid may flow into multi-channel chamber 702 through inlet channel 704a. A predetermined amount of liquid may be dosed into multi-channel chamber 702 via inlet channel 704a and 704b in succession using a similar process to that described with regard to FIG. 4A-C. In another embodiment, an amount of the first and second liquids is left behind in multi-channel chamber 702 using a similar process to that described with regard to FIGS. 6A-C. The amount of the first liquid left behind may correspond to the height $h_1$ of first opening 706a. Then, inlet channel 704a is closed off to the atmosphere while a second liquid flows into multi-channel chamber 702 through inlet channel 704b. Again, using a similar process already discussed, a predetermined amount of the second liquid is left behind in multi-channel chamber 702. The amount of the second liquid left behind may correspond to a difference between height $h_2$ and $h_1$ of opening 706b and 706a respectively.

It should be appreciated that although only two inlet channels are illustrated, any number of inlet channels may be realized to deliver liquids at various heights along the length of multi-channel chamber 702.

Figure 8:
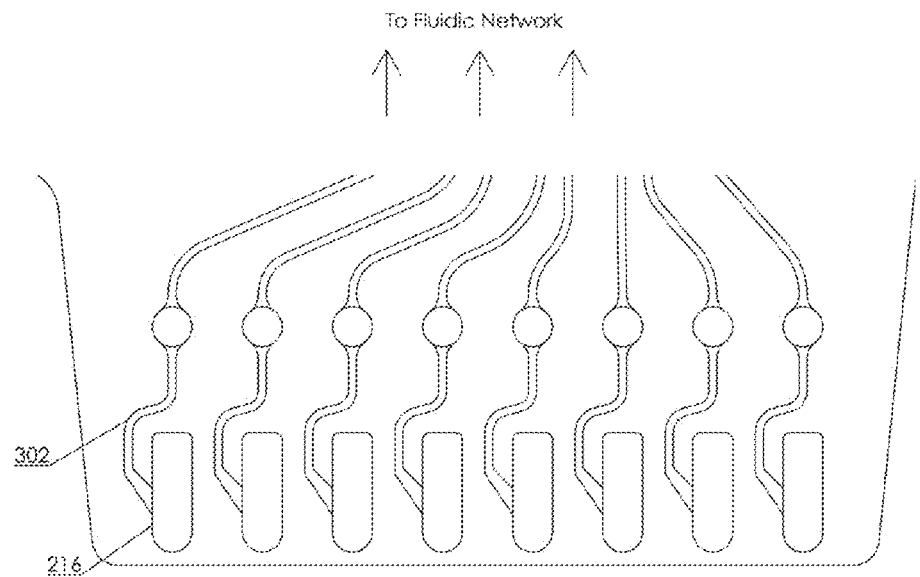
FIG. 8 illustrates another plurality of test chambers, according to an embodiment.

FIG. 8 illustrates a plurality of test chambers 216 as might be arranged in cartridge housing 102, according to another embodiment. Each test chamber 216 of the plurality includes an inlet channel 302. Each inlet channel 302 may further connect to a fluidic network, such as, for example, the fluidic network around test cartridge 102.

A single pressure source (not shown) may be coupled to the system to flow liquid down each of the plurality of inlet channels 302. Thus, each of the plurality of test chambers 216 can be filled with the same pressure source. Additionally, during the application of a negative pressure, the same predetermined amount of fluid may be left behind in each of the plurality of test chambers 216. The same amount of fluid may be left in each test chamber 216 regardless of any geometrical differences between the various inlet channels 302, since each test chamber 216 is similarly pressurized. In another example, liquid may be pressurized into each channel up until a liquid sensing area disposed in each channel to set a pre-determined amount of liquid in each channel, before dosing the liquid down into test chambers 216.

Figure 9:
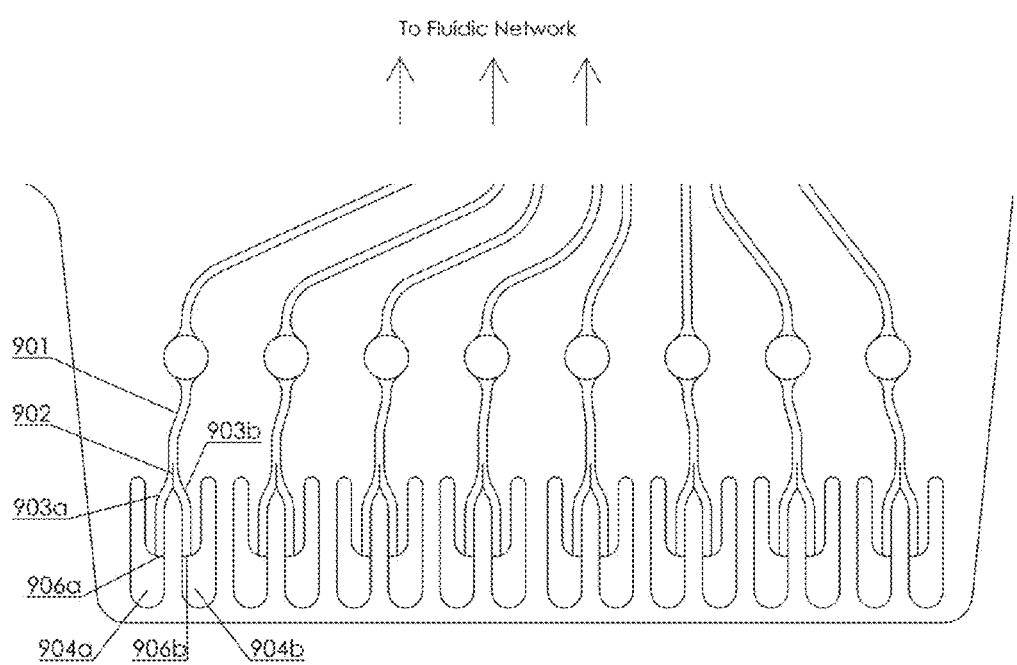
FIG. 9 illustrates another plurality of test chambers, according to an embodiment.

FIG. 9 illustrates a plurality of test chambers, according to another embodiment. Instead of each inlet channel 901 coupling to a single chamber, each inlet channel 901 includes a fluidic splitter 902 to divide liquid flow into at least two split channels 903a-b. The at least two split channels 903a-b may then couple to at least two test chambers 904a-b. Although each inlet channel is depicted in FIG. 9 as splitting into two split channels 903a-b, it would be understood by one having one skill in the relevant art(s) given the description herein how to split any of the inlet channels 901 into any number of other channels. Each of split channels 903a-b may couple to respective test chambers 904a-b via opening 906a-b disposed along a length of the respective test chamber. In one example, each inlet channel 901 may further connect to a fluidic network.

Feeding multiple test chambers from a fewer number of inlet channels helps to ensure that each test chamber contains the same concentrations of the compounds present within the liquid. Furthermore, using a single inlet channel to dose multiple test chambers reduces the complexity of coupling a single pressure source to control the fluid flow to each chamber.

Figure 10:
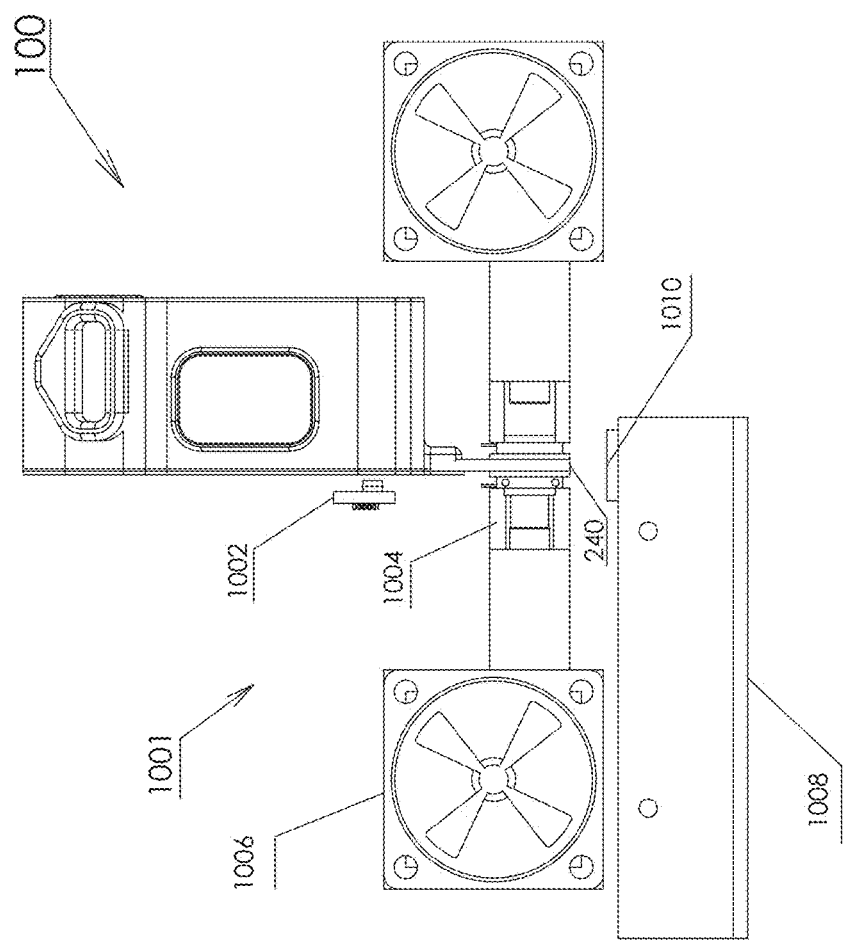
FIG. 10 illustrates the test cartridge system within an analyzer, according to an embodiment.

FIG. 10 illustrates an analyzer 1001 that operates to perform optical detection of compounds within test cartridge system 100, according to an embodiment. Analyzer 1001 includes an optical probe 1002, a temperature control element 1004, a fan 1006, and a photodetector unit 1008 that includes an objective 1010.

Optical probe 1002 may be aligned over channel enlargement 214 to detect the presence of liquid within the respective channel chamber. Optical probe 1002 may use infrared or visible light wavelengths and include any number of detectors and transmitter components. Additionally, the data collected from optical probe 1002 may be used to control other components of analyzer 1001. For example, after optical probe 1002 has detected that liquid has been present for a certain threshold period of time, a signal may be sent to stop applying a positive pressure to the liquid and/or begin heating the contents of the test chambers of test cartridge system 100 using temperature control element 1004.

Temperature control element 1004 may be disposed near the test chambers along the bottom portion of test cartridge system 100. Temperature control element 1004 may contain components to heat and/or cool the contents of the test chambers. For example, temperature control element 1004 may be a Peltier device that applies thermoelectric heating or cooling. In another example, temperature control element 1004 is a resistive heater. Current may be passed through coils of wire or strips of metal printed on a surface to heat the surrounding area. In yet another example, temperature control element 1004 provides forced air to either heat or cool the test chambers. The forced air may be provided by fan 1006. In an embodiment, analyzer 1001 has temperature control elements on both sides of the test chambers. One temperature control element may be used for heating while the other is used for cooling, for example.

Photodetector unit 1008 may contain any type of optical detector known to those skilled in the relevant art(s) including, but not limited to, CCD arrays, photodiodes, and CMOS sensors. In one embodiment, photodetector unit 1008 supplies an excitation wavelength of light to the test chambers and collects the emitted fluorescence light through objective 1010. In another embodiment, the excitation wavelength is supplied by another source (not shown). The emitted fluorescence escapes the test chambers via optical access area 240 along the bottom portion of the test chambers.

Figure 11:
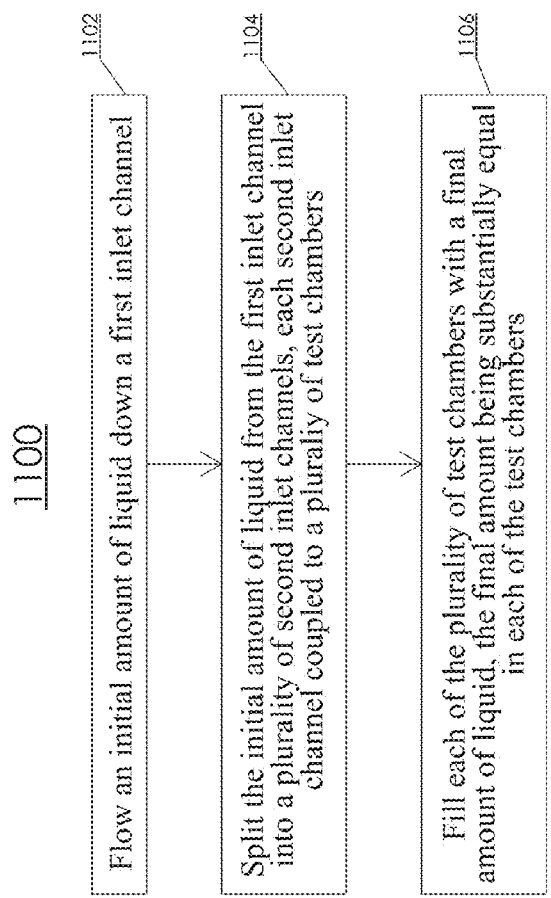

FIG. 11 is a flow chart illustrating a chamber filling method 1100, according to an embodiment.

At block 1102, an initial amount of liquid flows down a first inlet channel. The first inlet channel may be, for example, connecting inlet 502 illustrated in FIG. 5.

At block 1104, the initial amount of liquid is split into a plurality of second inlet channels, with each of the second inlet channels coupled to a plurality of test chambers. In an embodiment, each of the plurality of test chambers has only one opening disposed along a length of the chamber for receiving one of the second inlet channels. A length of each test chamber may be aligned substantially parallel to a gravity vector.

At block 1106, each of the plurality of test chambers is filled with a final amount of liquid that is substantially equal in each of the test chambers. Additionally, the final amount of liquid in each test chamber sums to equal the initial amount of liquid.

Other actions may be considered as well as part of chamber filling method 1100. For example, chamber filling method 1100 may include re-suspending one or more reagents disposed in one or more of the plurality of test chambers in the final amount of liquid dosed into each of the test chambers. Another example action includes heating the contents within at least one of the plurality of test chambers. The heating may be performed by, for example, a Peltier device, a resistive heating element, and/or forced air. One or more optical properties of the contents within at least one of the plurality of test chambers may also be detected during chamber filling method 1100.

Figure 12:
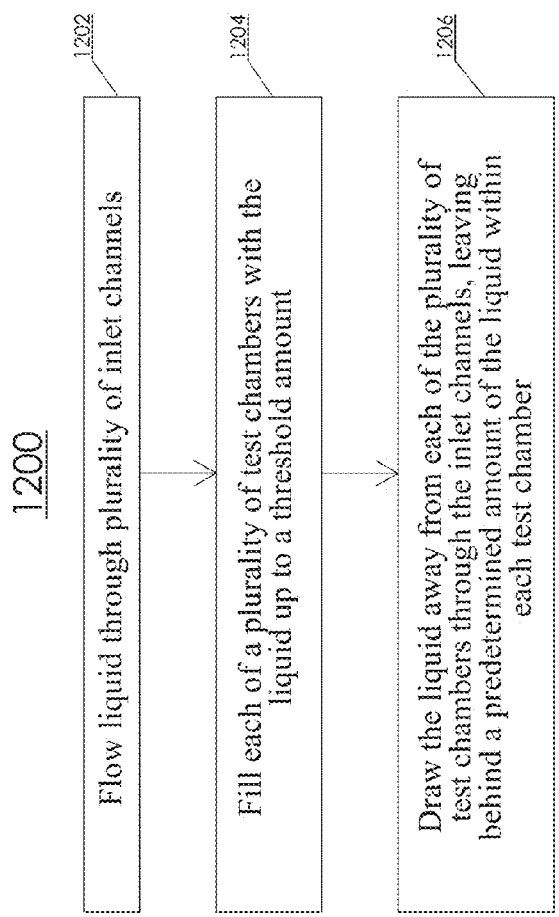

FIG. 12 is a flow chart illustrating a chamber filling method 1100, according to an embodiment.

At block 1202, liquid is flown through a plurality of inlet channels. Each of the inlet channels is coupled to a plurality of test chambers, according to an embodiment. A length of each test chamber is aligned substantially parallel to a gravity vector. In an embodiment, each of the plurality of test chambers has only one opening disposed along the length of the chamber. In one example, the flowing through the plurality of inlet channels is performed via a single pump source.

At block 1204, each of the plurality of test chambers is filled with the liquid up to a threshold amount. In one example, the threshold amount is equal to or greater than a height at which the opening is disposed along the length of each of the test chambers.

At block 1206, the liquid is drawn away from each of the plurality of test chambers through the inlet channels, leaving behind a predetermined amount of the liquid within each test chamber. The predetermined amount of liquid may be an amount of liquid that is below the height at which the opening is disposed along the length of each of the test chambers. For example, the amount of liquid left in the chamber may be determined by the point at which the gravitational force and surface tension on the liquid overcome the negative pressure applied to the channel.

Other actions may be considered as well as part of chamber filling method 1200. For example, chamber filling method 1200 may include re-suspending one or more reagents disposed in one or more of the plurality of test chambers in the amount of the liquid left behind within the one or more test chambers. If reagents are re-suspended, then the drawing of liquid in block 1206 is performed quickly enough such that the drawn liquid does not contain the reagents. Another example action includes heating the contents within at least one of the plurality of test chambers. The heating may be performed by, for example, a Peltier device, a resistive heating element, and/or forced air. One or more optical properties of the contents within at least one of the plurality of test chambers may also be detected during chamber filling method 1200.

Figure 13:
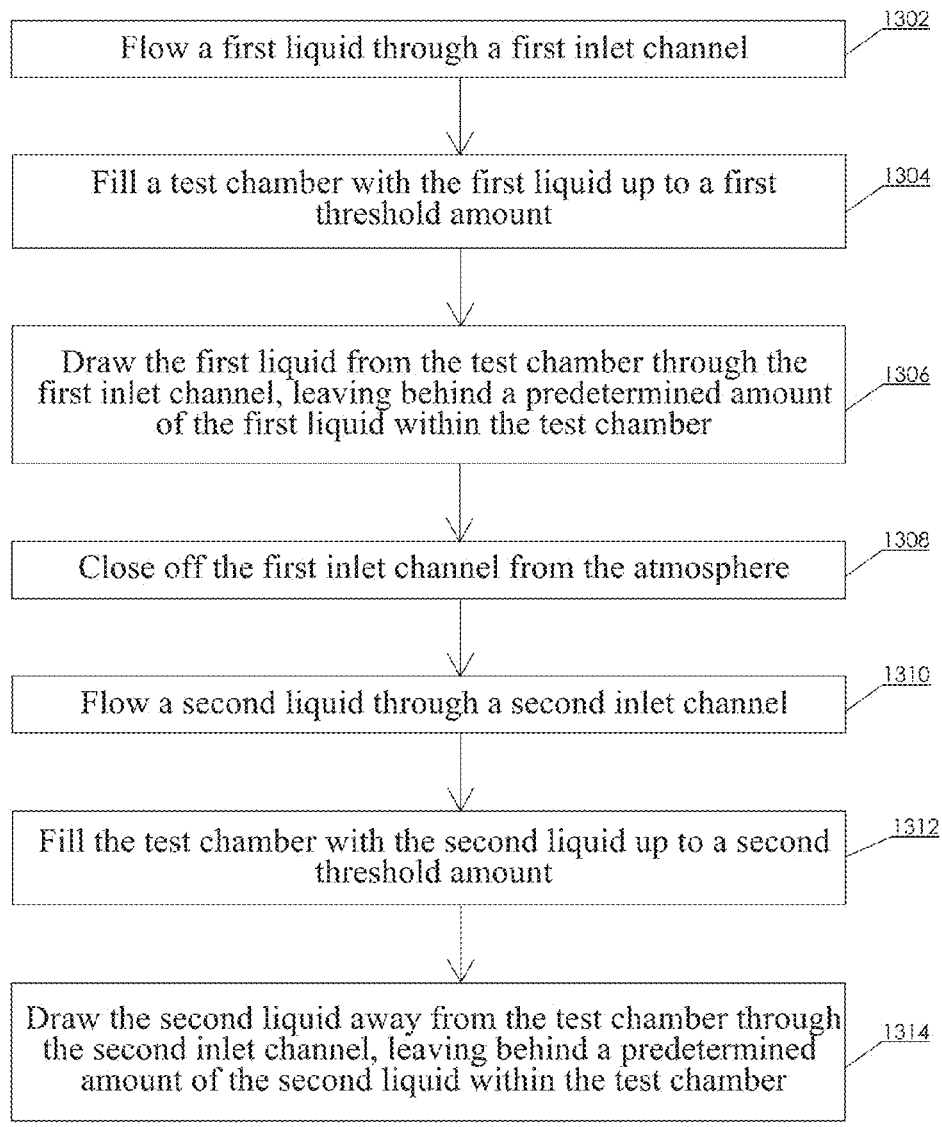

FIG. 13 is a flow chart illustrating another chamber filling method 1200, according to an embodiment.

At block 1302, a first liquid flows through a first inlet channel. In an embodiment, the first inlet channel is coupled to a first opening disposed along a length of a test chamber at a first height. The length of the test chamber is aligned substantially parallel to a gravity vector. While the first liquid flows through the first inlet channel at block 1302, a second inlet channel coupled to the test chamber is closed off to the atmosphere. In one example, both the first and second inlet channels are open to the atmosphere to start with.

At block 1304, the test chamber is filled with the first liquid up to a first threshold amount. In one example, the first threshold amount is equal to or greater than the first height of the first opening of the test chamber.

At block 1306, the first liquid is drawn away from the test chamber through the first inlet channel, leaving behind a first predetermined amount of liquid within the test chamber. The first predetermined amount of liquid may be an amount of liquid that corresponds to the first height of the first opening of the test chamber. For example, the amount of liquid left in the chamber may be determined by the point at which the gravitational force and surface tension on the liquid overcome the negative pressure applied to the first channel.

At block 1308, the first inlet channel is closed off to the atmosphere and the second inlet channel is opened, according to an embodiment. The switching of the active channel may be performed via one or more valves coupled to the fluidic network.

At block 1310, a second liquid flows through a second inlet channel. In an embodiment, the second inlet channel is coupled to a second opening disposed along the length of the test chamber at a second height that is greater than the first height. In one example, the flowing of both the first liquid in block 1302 and the second liquid in block 1308 is performed via a single pump source.

At block 1312, the test chamber is filled with the second liquid up to a second threshold amount.

At block 1314, the second liquid is drawn away from the test chamber through the second inlet channel, leaving behind a second predetermined amount of liquid within the test chamber. In one example, the second predetermined amount of liquid is an amount of liquid that corresponds to the difference between the second height of the second opening and the first height of the first opening of the test chamber. In another example, the amount of liquid left in the chamber may be determined by the point at which the gravitational force and surface tension on the liquid overcome the negative pressure applied to the second channel.

Similarly to chamber filling method 1200, other actions may be considered as part of chamber filling method 1300. For example, chamber filling method 1300 may include re-suspension of one or more reagents disposed within the test chamber in the predetermined amount of the first and second liquids left behind in the test chamber. Alternatively, the one or more reagents may be re-suspended in only the first liquid left behind in the test chamber. In one example, any reagents that may be present within the test chamber are not drawn back into either the first or second inlet channel in blocks 1306 and 1314 respectively. Chamber filling method 1300 may further include heating the contents of the test chamber and/or detecting one or more optical properties of the contents of the test chamber as described previously in regards to chamber filling method 1200. Although only two inlet channels are described in chamber filling method 1300, it should be appreciated that chamber filling method 1300 may be expanded to include any number of inlet channels into one or more chambers.

FIG. 14 is a flow chart illustrating another chamber filling method 1400, according to an embodiment.

At block 1402, a liquid flows through each of a plurality of channels up to a liquid sensing area disposed in each channel, according to an embodiment. The liquid may be pressurized to flow down each channel, and may be flown down each channel separately or simultaneously. Flowing the liquid up to the sensing area sets a pre-determined amount of liquid within each of the plurality of channels, according to an embodiment.

At block 1404, the pre-determined amount of liquid within each of the plurality of channels flows into respective chambers coupled to each of the channels, according to an embodiment. Each channel may be separately or simultaneously pressurized to force the pre-determined amount of liquid down into each corresponding chamber.

Method 1400 may also include re-suspending one or more reagents disposed in one or more channels of the plurality of channels. The reagents may be disposed within premixing chambers coupled to each of the channels.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Embodiments of the present invention have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The Summary and Abstract sections may set forth one or more but not all exemplary embodiments of the present invention as contemplated by the inventor(s), and thus, are not intended to limit the present invention and the appended claims in any way.

The breadth and scope of the present invention should not be limited by any of the above-described exemplary embodiments, but should be defined only in accordance with the following claims and their equivalents.

What is claimed is:

1. A method comprising:
    flowing liquid through a plurality of inlet channels, each inlet channel coupled to a corresponding test chamber of a plurality of test chambers via an opening through a wall of the corresponding test chamber, wherein the wall defines a longest side of the corresponding test chamber, and wherein the opening is the only opening into the corresponding test chamber;
    filling each of the plurality of test chambers with the liquid up to a threshold amount;
    drawing the liquid away from each of the plurality of test chambers through the opening of each corresponding test chamber, wherein the drawing leaves behind a predetermined amount of the liquid below a height at which the opening is disposed along the wall of each corresponding test chamber.

2. The method of claim 1, further comprising re-suspending one or more reagents disposed in one or more of the plurality of test chambers in the predetermined amount of the liquid left behind within the one or more test chambers.

3. The method of claim 2, wherein the drawing draws liquid that does not contain the one or more reagents.

4. The method of claim 1, wherein filling up to the threshold amount comprises filling each of the test chambers up to a height equal to or greater than a height at which the opening is disposed along the wall of each corresponding test chamber.

5. The method of claim 1, further comprising heating the liquid within at least one of the plurality of test chambers.

6. The method of claim 5, wherein the heating comprises heating with a Peltier device.

7. The method of claim 5, wherein the heating comprises heating with resistive heating elements.

8. The method of claim 5, wherein the heating comprises heating with forced air.

9. The method of claim 1, further comprising detecting one or more optical properties of contents in the liquid within at least one of the plurality of test chambers.

10. The method of claim 1, wherein the flowing is performed via a single pump source.

* * * * *